United States Patent [19]

Schaffer

[11] 4,387,072
[45] Jun. 7, 1983

[54] NOVEL PALLADIUM ALLOY AND DENTAL RESTORATIONS UTILIZING SAME

[75] Inventor: Stephen P. Schaffer, Bloomfield, Conn.

[73] Assignee: The J. M. Ney Company, Bloomfield, Conn.

[21] Appl. No.: 371,801

[22] Filed: Apr. 27, 1982

[51] Int. Cl.$^3$ .............................................. C22C 5/04
[52] U.S. Cl. .................................... 420/463; 420/464
[58] Field of Search ...................... 75/172 R, 172 G; 433/207, 222; 420/463, 464

[56] References Cited

U.S. PATENT DOCUMENTS

| | | | |
|---|---|---|---|
| 2,050,077 | 8/1936 | Wise | 75/134 C |
| 2,105,312 | 1/1938 | Cohn | 75/172 R |
| 2,132,116 | 10/1938 | Kiepe | 75/172 R |
| 2,143,217 | 1/1939 | Truthe | 75/135 |
| 3,134,671 | 5/1964 | Prosen | 75/172 G |
| 3,438,770 | 4/1969 | Clark et al. | 75/134 V |
| 3,819,366 | 6/1974 | Katz | 75/172 R |
| 3,989,515 | 11/1976 | Reiff | 75/172 R |
| 4,063,937 | 12/1977 | Goltsov et al. | 75/172 G |
| 4,179,286 | 12/1979 | Knosp | 75/134 N |
| 4,179,288 | 12/1979 | Prosen | 75/172 R X |

Primary Examiner—L. Dewayne Rutledge
Assistant Examiner—David A. Hey

[57] ABSTRACT

A palladium alloy for use in making porcelain coated dental restorations comprises 50–85 percent palladium, 5–40 percent copper and/or cobalt, 1–15 percent gallium, up to 5 percent of a modifier selected from nickel, gold, indium, ruthenium and tin, up to 0.5 percent rhenium and/or iridium, and up to 1 percent boron. The dental restorations obtained by firing porcelain against castings of this alloy exhibit freedom from discoloration, and excellent bond strength is obtained between the porcelain coating and the underlying alloy casting.

11 Claims, No Drawings

NOVEL PALLADIUM ALLOY AND DENTAL RESTORATIONS UTILIZING SAME

BACKGROUND OF THE INVENTION

As is well known, dental casting alloys should provide a high degree of biocompatibility or inertness to the conditions in the mouth and good physical properties so that they will provide long lived usage. In addition, those alloys which are used to provide castings upon which porcelain coatings may be cast must provide good bonding characteristics to the porcelain coatings and other characteristics which are compatible with the porcelain coatings, such as similar coefficient of expansion, avoidance of discoloration of the porcelain, etc. Lastly, the alloy should process well during casting and be useful with commercially available porcelains.

Until recent years, gold alloys, usually gold/platinum alloys, have been preferred as dental casting materials because they have provided a highly desirable balance of properties. The commercially available dental porcelains have been formulated so as to be compatible therewith.

Recently, the escalating costs of gold and platinum have resulted in extensive efforts to find alternate alloy compositions which would afford acceptable properties at considerably lower cost. Base metal alloys have generally been found to suffer from one or more limitations such as lack of sufficient biocompatibility, lack of aesthetics, etc. As a result, over the last several years, there has been considerable activity in the development of palladium base alloys in an effort to make use of the nobility of lower cost palladium.

A number of palladium/silver alloys have been developed which simulate the appearance of platinum alloys and which provide a high degree of biocompatibility while still exhibiting useful casting and physical properties. However, the silver content has a tendency to oxidize at the porcelain firing temperature and to discolor the porcelains being fired thereon to provide the aesthetic coatings which are widely employed, particularly in anterior dental restorations. In applicant's copending application Ser. No. 174,759 filed Aug. 4, 1980, there is disclosed a palladium/silver alloy which has overcome much of the discoloration problem.

However, even the palladium/silver alloys of applicant's copending application require close control in the porcelain firing step and selection of the porcelains used in connection therewith. The generally available dental porcelains were formulated for use with high gold content alloys so as to exhibit a coefficient of thermal expansion which is typically 5–10 percent lower than the high gold content alloys. This results in placing the porcelain coating in compression after cooling from the firing temperature, thereby producing a stronger restoration when it is subjected to tensile loading.

The reduction or elimination of the gold content in some of the substitute alloys has caused difficulty in maintaining a sufficiently high thermal coefficient of expansion, which is desirably in the range of 0.66–0.72 percent at 500° C. As indicated in applicant's above identified copending application, silver has been used to replace gold in an effort to provide a suitable coefficient of expansion but it readily oxidizes at the porcelain firing temperatures. The silver oxide then diffuses into the porcelain and undergoes ion exchange with sodium therein to produce a distinct uncontrolled discoloration of the porcelain which is aesthetically unacceptable.

Alloys for use as ceramo-metal restorations must also exhibit a desired balance of physical and mechanical properties The hardness must exceed 150 Vickers to withstand the abrasion of opposing teeth. To withstand the stress transmitted through the restoration, the alloy must have an offset yield strength at 0.1 percent of over 40,000 psi. Tensile elongation of at least 6 percent is required to allow the margins of the alloy to be adjusted after being placed in the patient's mouth.

Moreover, a dental casting alloy must be able to be soldered before the porcelain firing cycle. Since porcelain is fired at approximately 1000° C., the alloy must possess a solidus of at least 1100° C. to allow the solder to flow without starting to melt the casting. However, in order to allow the alloy to be cast with standard equipment found in dental laboratories, the liquidus temperature must not be greater than 1400° C. Lastly, the alloy must also exhibit good bonding to dental porcelains which is represented by a minimum value for the maximum bending stress of 12,000 psi and a minimum value for the bending strength ratio (maximum bending stress/modulus of elasticity of the alloy) of $0.7 \times 10^{-3}$.

It is an object of the present invention to provide a novel palladium dental alloy which exhibits a highly desirable balance of casting properties and physical properties, together with biocompatibility and freedom from discoloration of porcelain coatings which are fired thereon and which provide good bonding of the porcelain coatings fired thereon.

It is also an object to provide such an alloy which is relatively inexpensive when compared to gold and platinum alloys and which provides a balance of properties which is comparable thereto.

Another object is to provide such an alloy which may be cast and soldered relatively easily and which will provide excellent bonding to porcelain coatings fired thereon and avoid discoloration thereof.

A further object is to provide dental restorations comprising castings of such alloys and procelain coatings fired thereon, and wherein the porcelain coatings are essentially free from any discoloration and exhibit a high degree of bonding strength to the casting.

SUMMARY OF THE INVENTION

It has now been found that the foregoing and related objects may be readily attained in a palladium alloy which consists essentially of, on a weight basis, 50–85 percent palladium; 5–40 percent of at least one metal selected from the group consisting of copper and cobalt; 1–15 percent gallium; up to 5 percent of a modifier selected from the group consisting of nickel, gold, indium, ruthenium, tin and mixtures thereof; up to 1 percent boron; and up to 0.5 percent of a grain refiner selected from the group consisting of rhenium and iridium.

In addition, the alloy may optionally contain up to 0.5 percent by weight of a grain refining component selected from the group consisting of rhenium, iridium and mixtures thereof.

Preferably, the alloys have a boron content of 0.1–0.5 percent and utilize gold as the modifier in an amount of 1–3 percent by weight. Copper is preferred over cobalt because of cost, and the copper and/or cobalt is desirably used in an amount of 5–15 percent. The palladium content is desirably in the range of 70–82 percent by weight of the alloy. Rhenium and/or iridium is provided as a grain modifier in about 0.05–0.2 percent.

A highly advantageous alloy is one containing 76–80 percent palladium, 9–12 percent copper and/or cobalt, 8–11 percent gallium, 0.2–0.35 percent boron, 1–3 percent of the modifier which is preferably gold, and 0.05–0.2 percent rhenium.

The dental restorations comprise a casting of the aforementioned alloy and a porcelain coating fired upon a portion of the casting. The porcelain coatings are substantially free from discoloration and are firmly bonded to the casting.

DETAILED DESCRIPTION OF THE PREFERRED EMBODIMENTS

As hereinbefore indicated the alloys of the present invention use palladium as the principal component, and use copper and/or cobalt, and gallium as the other essential components. They desirably contain a small amount of boron and a small amount of selected modifying elements. In addition, they may contain as grain refining components, rhenium and/or iridium.

The alloys must contain at least 50 percent palladium and may contain as much as 85 percent palladium. Preferably, the alloy contains 70–82 percent palladium in order to obtain the desired nobility and an optimum balance of properties.

The copper and/or cobalt content may vary from 5–40 percent by weight of the total composition and is preferably in the range of 5–15 percent by weight. This component reduces the melting point of the alloy while maintaining a single phase solid solution microstructure.

To provide both hardness to the alloy and the necessary oxide formation to effect bonding with the porcelain coating, gallium must be used in an amount of 1–15 percent and preferably in the range of 3–12 percent. Amounts above 15 percent will tend to adversely affect other properties.

Boron is desirably added in the range of 0.1–1. percent and preferably in the range of 0.1–0.5 to improve the hardness and serve as a scavenger for oxides formed in the alloy during the casting process.

The group of modifier metals comprised of nickel, gold, indium, ruthenium, tin, and mixtures thereof is utilized in the range of up to 5 percent to prevent discoloration of the porcelain during firing while having some minor benefits on the desired coefficient of thermal expansion. Amounts of as little as 0.3 percent have been found to provide significant benefits. Generally, amounts in excess of 3.0 percent provide no additional benefit, and amounts in excess of 5 percent adversely affect the balance of properties of the alloy and should not be employed. Preferably, gold is used in the amount of 1–3 percent.

For most applications, it is desirable to incorporate rhenium and/or iridium in an amount of up to 0.5 percent by weight in order to effect grain refinement. When such a grain refining component is included, it is preferably present in the range of 0.05–0.15 percent. However, desirable casting and other properties have been obtained without the incorporation of a grain refining component.

The alloys produced in accordance with the present invention routinely exhibit a hardness in excess of 150 Vickers, which is necessary to withstand the abrasion of opposing teeth. Because the porcelain coating is fired at about 1000° C., the solidus temperature is in excess of 1100° C., the liquidus temperature of the alloy is well below 1400° C. to permit facile processing in the equipment generally available in dental laboratories. To provide a good compatible alloy for use with present commercial porcelains, the alloy has a coefficient of thermal expansion within the range of 0.65–0.72 percent at 500° C. The yield strength of the alloy at 0.1 percent is in excess of 50,000 psi, and the tensile elongation of the alloy is in excess of 6 percent to permit the margins of the casting to be adjusted in the mouth of the patient. Moreover, the alloys of the present invention have both high corrosion resistance and tarnish resistance and they do not discolor the porcelain.

Illustrative of the efficacy of the alloys of the present invention are the following examples, wherein all parts are parts by weight unless otherwise indicated.

EXAMPLE ONE

An alloy is prepared containing 78.65 percent palladium, 10.0 percent copper, 9.0 percent gallium, 2.0 percent gold, 0.25 percent boron, and 0.10 percent rhenium.

Specimens cast therefrom are found to exhibit a Vickers hardness of 440 and to have an offset yield strength at 0.1 percent of 142,000 psi. The tensile elongation is 14 percent.

Several commercial porcelains available from different manufacturers are fired against castings of this alloy in accordance with the manufacturers' specifications. In all instances, the bond strength is excellent and the fired restorations are found to be free from any discoloration of the porcelain. Exposure to corrosion testing of the cast sample indicates freedom from tarnish.

EXAMPLE TWO

A second alloy is prepared with the same composition as that of Example One but substituting iridium for the rhenium.

This alloy is found to have a solidus temperature of 1170° C. and a liquidus temperature of 1190° C. Specimens cast therefrom exhibit a Vickers hardness of 423 and an offset yield strength at 0.1 percent of 166,000 psi. The tensile elongation is 8 percent, and the coefficient of thermal expansion at 500° C. is 0.680.

When commercially available porcelains are cast thereagainst, the bond strength ratio is found to be $1.48 \times 10^{-3}$ and the maximum bending stress is found to be 20,200 psi (1420 Kg/cm$^2$).

EXAMPLE THREE

To test the effect of using different modifying elements, a series of alloys are prepared using 2.0 percent by weight of the potential modifying element, and castings thereof are tested. The alloy formulation and physical test data are set forth in Table One.

Columbium (niobium) has been found unacceptable because of excessive depression of the coefficient of expansion.

TABLE ONE

|    | A    | B    | C    | D    | E    |
|----|------|------|------|------|------|
| Pd | 78.0 | 78.0 | 78.0 | 80.0 | 80.0 |
| Co | —    | —    | —    | —    | 20.0 |
| Cu | 20.0 | 20.0 | 20.0 | 20.0 | —    |
| Ga | —    | —    | —    | —    | —    |
| Ru | —    | —    | —    | —    | —    |
| B  | —    | —    | —    | —    | —    |
| Sn | 2.0  | —    | —    | —    | —    |
| In | —    | 2.0  | —    | —    | —    |
| Nb | —    | —    | 2.0  | —    | —    |

TABLE ONE-continued

|  | A | B | C | D | E |
|---|---|---|---|---|---|
| Au | — | — | — | — | — |
| Expansion | .657 | .670 | .637 | .655 | .787 |
| Hardness (HV) | 128 | 118 | 161 | 94 | 105 |
| Yield Strength × 10³, psi | — | 45 | 63 | 20 | — |

EXAMPLE FOUR

To test the effect of varying the gallium content, a series of alloys are prepared, and cast specimens thereof are tested. The formulations and the physical test data are set forth in Table Two.

TABLE TWO

|  | A | B | C | D |
|---|---|---|---|---|
| Pd | 75.0 | 78.0 | 84.0 | 77.0 |
| Co | — | — | — | — |
| Cu | 10.0 | 10.0 | 10.0 | 20.0 |
| Ga | 15.0 | 12.0 | 6.0 | 3.0 |
| Ru | — | — | — | — |
| B | — | — | — | — |
| Sn | — | — | — | — |
| In | — | — | — | — |
| Nb | — | — | — | — |
| Au | — | — | — | — |
| Expansion | .695 | .673 | .659 | .652 |
| Hardness (HV) | 435 | 424 | 180 | 155 |
| Yield Strength × 10³, psi | — | 154 | — | 69 |

EXAMPLE FIVE

To determine the value of the boron component, an alloy of 80.5 percent palladium, 10.0 percent copper, 9.0 percent gallium, and 0.5 percent boron is prepared, and test specimens are cast therefrom. This alloy exhibits a thermal expansion value of 0.628, Vickers hardness of 472 and maximum yield strength at 0.1 percent of 152,000 psi.

A second alloy formulation containing 81.0 percent palladium, and the same amount of copper and gallium, but no boron, is prepared and test specimens are cast therefrom. This alloy exhibits a thermal expansion value of 0.651, Vickers hardness of 424 and yield strength of 154,000 psi.

The preferred alloys balance the depressing effect on thermal expansion by adjustment of other components since the boron does provide desirable benefits in hardness and as a scavenger.

EXAMPLE SIX

To test the effect of varying the gallium content in an alloy containing a high content of copper and cobalt combined, two alloy formulations are prepared, each containing 10.0 percent copper and 10.0 percent cobalt. In the first, the palladium content is 68.0 percent and the gallium content is 12.0 percent. In the second, the palladium content is 74.0 percent and the gallium content is 6.0 percent.

Upon testing cast specimens of the two alloy formulations, the following results are obtained.

| Test | First Alloy | Second Alloy |
|---|---|---|
| Thermal Expansion | .707 | .729 |
| Vickers Hardness | 354 | 258 |
| Offset Yield Strength, psi | — | 68,000 |

EXAMPLE SEVEN

To test the effect of omitting copper and cobalt, an alloy is prepared containing 85.0 percent palladium, 11.6 percent gallium, 3.0 percent gold, 0.3 percent boron and 0.1 percent iridium. Specimens cast therefrom exhibit an offset yield strength at 0.1 percent of 120,000 psi and Vickers hardness of 340.

Thus, it can be seen from the foregoing detailed specification and examples that the alloys of the present invention provide a highly desirable balance of properties for use with dental porcelains including good casting characteristics, good physical properties, high tarnish resistance, solderability, and substantial elimination of any tendency for discoloration of porcelain coatings fired thereon. The alloys may be processed readily using available dental laboratory equipment and may be used with currently available commercial porcelains. The result is highly attractive, useful and long lived dental restorations.

I claim:
1. A dental alloy consisting essentially of:
   a. 50–85 percent by weight palladium;
   b. 5–40 percent by weight of at least one metal selected from the group of cobalt and copper;
   c. 1–15 percent by weight gallium;
   d. up to 5 percent by weight of a modifier selected from the group consisting of nickel, gold, indium, ruthenium, tin and mixtures thereof;
   e. up to 1 percent by weight boron; and
   f. up to 0.5 percent by weight of a grain refiner selected from the group consisting of rhenium, iridium, and mixtures thereof, said alloy having a thermal expansion of about 0.66–0.72 percent at 500° C., a solidus temperature of at least 1100° C., a liquidus temperature of not more than 1400° C., Vickers hardness greater than 150, offset yield strength at 0.1 percent of greater than 40,000 p.s.i., and tensile elongation greater than 6 percent.

2. The dental alloy of claim 1 wherein the boron content is 0.1–0.5 percent.

3. The dental alloy of claim 1 wherein the palladium content is 7–82 percent, the cobalt and/or copper content is 5–15 percent, the gallium content is 3–12 percent, and the modifier content is 1–3 percent.

4. The dental alloy of claim 3 wherein the boron content is 0.1–0.5 percent.

5. The dental alloy of claim 4 wherein the modifying element is gold.

6. The dental alloy of claim 1 wherein the palladium content is 76–80 percent, the cobalt and/or copper content is provided by copper in the amount of 9–12 percent, the gallium content is 8–11 percent, the modifying element is provided by gold in the amount of 1–3 percent, the boron content is 0.2–0.35 percent; and the grain refiner comprises 0.05–0.15 percent thereof.

7. A dental restoration comprising:
   a. a casting of a dental alloy consisting essentially of (i) 50–85 percent by weight palladium, (ii) 5–40 percent by weight of at least one metal selected from the group of cobalt and copper, (iii) 1–15 percent by weight gallium, (iv) up to 5 percent by weight of a modifier selected from the group consisting of nickel, gold, indium, ruthenium, tin and mixtures thereof, (v) up to 1 percent by weight boron, and (vi) up to 0.5 percent by weight of a grain refiner selected from the group consisting of rhenium, iridium, and mixtures thereof, said alloy having a thermal expansion of about 0.66–0.72 percent at 500° C., a solidus temperature of at least 1100° C., a liquidus temperature of not more than 1400° C. Vickers hardness greater than 150, offset yield strength at 0.1 percent of greater than 40,000 p.s.i., and tensile elongation greater than 6 percent; and b. a porcelain coating upon a portion of said casting, said coating being firmly bonded to said casting and being substantially free from discoloration, the bond of said coating to said casting having a minimum value for maximum bending strength of 12,000 p.s.i. and a minimum value for the bending strength ratio of $0.7 \times 10^{-3}$.

8. The dental restoration of claim 7 wherein the boron content of said alloy is 0.1–0.5 percent by weight thereof.

9. The dental restoration of claim 7 wherein said alloy contains 70–82 percent by weight palladium, 5–15 percent by weight cobalt and/or copper, 3–12 percent by weight gallium, 1–3 percent by weight of the modifier, and 0.05–0.15 percent by weight of the grain refiner.

10. The dental restoration of claim 9 wherein the boron content of said alloy is 0.1–0.5 percent by weight thereof.

11. The dental restoration of claim 10 wherein the modifying element is gold.

* * * * *

UNITED STATES PATENT AND TRADEMARK OFFICE
CERTIFICATE OF CORRECTION

PATENT NO. : 4,387,072
DATED : June 7, 1983
INVENTOR(S) : Stephen P. Schaffer

It is certified that error appears in the above—identified patent and that said Letters Patent is hereby corrected as shown below:

Column 6, line 43, "7-82 percent" should be -- 70-82 percent --

Signed and Sealed this

Fourteenth Day of February 1984

[SEAL]

Attest:

GERALD J. MOSSINGHOFF

Attesting Officer

Commissioner of Patents and Trademarks